United States Patent
Liebrecht et al.

(10) Patent No.: US 6,778,861 B1
(45) Date of Patent: Aug. 17, 2004

(54) BONE SCREW COMPRISING A DEVICE FOR ELECTROSTIMULATION

(75) Inventors: Felix Liebrecht, München (DE); Werner Kraus, München (DE); Heribert Stephan, München (DE)

(73) Assignee: Geot Gesellschaft fur Elektro-Osteo-Therapie G.m.b.H., Munich (DE)

( * ) Notice: Subject to any disclaimer, the term of this patent is extended or adjusted under 35 U.S.C. 154(b) by 84 days.

(21) Appl. No.: 10/018,937
(22) PCT Filed: Jun. 21, 2000
(86) PCT No.: PCT/EP00/05780
§ 371 (c)(1), (2), (4) Date: May 10, 2002
(87) PCT Pub. No.: WO01/00097
PCT Pub. Date: Jan. 4, 2001

(30) Foreign Application Priority Data

Jun. 23, 1999 (DE) .......................................... 199 28 449

(51) Int. Cl.[7] .................................................. A61N 1/05
(52) U.S. Cl. .......................... 607/116; 607/51; 607/149; 606/73
(58) Field of Search .............................. 607/51, 50, 116, 607/149, 117; 606/72, 73, 32, 41

(56) References Cited

U.S. PATENT DOCUMENTS

| | | | | |
|---|---|---|---|---|
| 4,195,367 A | * | 4/1980 | Kraus | 623/23.49 |
| 5,292,252 A | * | 3/1994 | Nickerson et al. | 433/173 |
| 5,496,256 A | * | 3/1996 | Bock et al. | 601/2 |
| 5,725,377 A | * | 3/1998 | Lemler et al. | 433/173 |
| 6,034,295 A | * | 3/2000 | Rehberg et al. | 623/23.49 |
| 6,120,502 A | * | 9/2000 | Michelson et al. | 606/61 |

FOREIGN PATENT DOCUMENTS

| | | |
|---|---|---|
| DE | 26 36 818 A1 | 2/1978 |
| DE | 31 32 488 A1 | 2/1983 |
| DE | 39 42 735 A1 | 6/1991 |
| DE | 4230181 A1 * | 3/1994 ............ A61B/5/04 |

OTHER PUBLICATIONS

Dee, R. et al., "Principles of Internal Fixation," *Principles of Orthopedic Practice*, McGraw–Hill, New York 1988, pp. 287–348.

* cited by examiner

Primary Examiner—Kennedy Schaetzle
(74) Attorney, Agent, or Firm—Duane Morris LLP

(57) ABSTRACT

Bone screw (10a) having a hollow, tubular shaft (12a) consisting of metal, such as titanium, the shaft having a head (14a) at one end and a self-tapping external thread (18a) at the other end. The head (14a) has a hexagonal recess (16a) for inserting a turning tool. An electrically insulated metallic end-piece (20a) which tapers in the direction of the end in the form of a cone or pointed arch, is inserted the other end of the shaft (12a). A receiving coil (30a) is located in the hollow shaft (12a), the terminals (36a, 38a) of the coil being electrically coupled to the shaft (12a) and to the end-piece (20a). The space between the end-piece (20a) and the end of the shaft (12a) as well as the interior of the shaft (12a) are filled with a biocompatible insulating compound (26a), such as an epoxy resin. A low-frequency electric voltage can be induced in the receiving coil by an external primary coil which is coupled to an oscillation generator. The electric voltage generates a growth-promoting current in the surrounding tissue, the shaft and the end-piece acting as tissue electrodes (stimulation method according to Kraus and Lechner).

6 Claims, 5 Drawing Sheets

BONE SCREW COMPRISING A DEVICE FOR ELECTROSTIMULATION

The present invention relates to a bone screw which comprises a device for electrostimulation.

It is known that the growth of tissue can be promoted by a low-frequency, essentially sinusoidal alternating current (Method according to Kraus and Lechner). It is known, for applying the alternating current to the region of the tissue to be stimulated, to implant an electric coil ("receiving coil") the terminals of which being coupled to electrodes ("tissue electrodes") applied to the tissue region to be stimulated. An electric voltage is induced in the receiving coil by means of an external primary coil coupled to an oscillation generator, said voltage being applied via said electrodes to the tissue region to be attended (DE-A-31 32 488).

The receiving coil may be housed in an intramedullary nail, the surface of which being provided with tissue electrodes (DE-A-31 32 488). It is further known, to couple the terminals of a receiving coil by snap-fastener-like connecting means to bone screws serving for osteosynthesis or only as electrodes (DE-A-39 42 735). A bone screw is also know which contains a rod-shaped permanent magnet.

The present invention is based on the task, to provide a bone screw with a device for electrostimulation which is easily to apply, safe in use and versatile.

A femur head prosthesis is known from document EP-A-0 781 532 comprising a shaft which has an interior cavity and holes which lead from the cavity to the exterior. The upper end of the shaft has a threaded hole for screwing-on an extraction tool, said hole being adapted to be closed by a drive-in screw. The cavity serves for receiving spongiosa into which the tissue surrounding the shaft should grow through the holes. To enhance the growing-in of the tissue, the drive-in screw is replaced by an electrifying device. This device has a hexagonal head, an adjacent thread fitting into the threaded hole, and a shaft protruding into the cavity. The shaft contains a receiving coil connected to electrodes so that a low-frequency electric current stimulating the growth of tissue can be induced in the cavity. This electrifying device is neither intended nor suited to be used as bone screw, because it would not be able to withstand the stresses to which a bone screw is subjected. Further the machine-screw thread, which must match the threaded hole, is not suited for a bone screw because of its configuration and position.

Dental implants are known from documents U.S. Pat. Nos. 5,292,252 and 5,725,377 which have a shaft with an external thread and a interior threaded hole at the upper end for fixing a tooth prostesis. A stimulator cap containing a battery is screwed into the threaded hole. In one embodiment, the battery is connected to a coil positioned in the shaft to produce a magnetic d.c. field in the surrounding at the implant. In other embodiments, the battery is connected to the shaft and to an electrode positioned on the front side of the stimulator cap. These dental implants are not suited for use as bone screws as they are needed for fixing osteosythesis plates or for connecting bone fragments.

An implant for electrostimulation of tissue is disclosed in document DE-A-42 30 181 which comprises a receiving coil in which a low-frequency electric voltage can be induced as described in document DE-A-31 32 488 mentioned above. The receiving coil is coupled by means of flexible leads to connectors for contacting conventional bone screws or tissue electrodes.

It is an object of the present invention to provide a device for electrostimulation of tissue by a low-frequency electric alternating current which can be used exactly like a conventional bone or cortical screw and in addition to its mechanical function produces an effective electrostimulation of the surrounding tissue.

This object is obtained according to the present invention by a bone screw comprising a tubular shaft made of biocompatible, electrically conductive material, said shaft having a head at a first end, said head having a configuration adapted to be engaged by a turning tool;

an end-piece made of biocompatible electrically conductive material positioned near a second end of said shaft;

an electric insulation between shaft and end-piece;

a receiving coil in said shaft in which coil a low-frequency electric alternating voltage can be induced by means of an external coil, first and second terminals of said receiving coil being electrically coupled to said shaft and said end-piece, respectively; and a bone-scew-type external thread positioned near the end of said shaft remote from said head Advantegous embodiments of the invention further exhibit one or several of the following features: The end-piece has a front portion with a rod-shaped extension inserted insulatedly in the second end of the shaft. Electrically insulating ring-shaped means is positioned between the extension and the shaft and an electrically insulating material is provided between the second end of the shaft and the front portion. The end-piece tapers with increasing distance from the shaft. The external thread is positioned on the shaft near the second end thereof and spaced therefrom or adjacent the second end or on the end-piece. The bone screw, a core of the receiving coil, the end-piece and the insulating material have an axial channel through which a guide wire can be put. The bone screw can comprise two parts, i. e. it comprises a tubular screw portion and an insert fitting into it, the insert comprising the end-piece and the receiving coil. Further features and benefits of the invention will become apparent from the following description.

A bone screw according to a first preferred embodiment of the invention has a hollow tubular shaft with a head at one end and a self-tapping external thread at the other end. The head has, as usual, an hexagonal hole for inserting a turning tool. An electrically insulated end-piece which tapers toward the end in form of a cone or a pointed arch is inserted in the other end. A receiving coil is located in the hollow shaft, the terminals of the coil being electrically coupled to the shaft and the end-piece. The space between the end-piece and the end of the shaft, and the interior of the shaft are filled by casting with a biocompatible insulating compound, such as an epoxy resin.

The present bone screw can be applied easily like a conventional bone screw. The connection between the receiving coil and the parts serving as electrodes, i. e. the shaft and the end-piece, is mechanically and electrically safe, because it is located within the interior of the shaft filled with insulating matter. The taper of the end-piece facilitates any later extraction. The bone screw of the invention can be used for many indications, e. g. avascular necrosis of the head of femur, osteochondrosis dissecans, vertebral ankylosis, and in combination with additional conventional bone screws for fixing an intra-articular fracture of the femur neck.

The invention is further explained with reference to the accompagnying drawings in which FIG. 1 is a longitudinal section of a bone screw according to a first embodiment of the invention;

Figure 1:
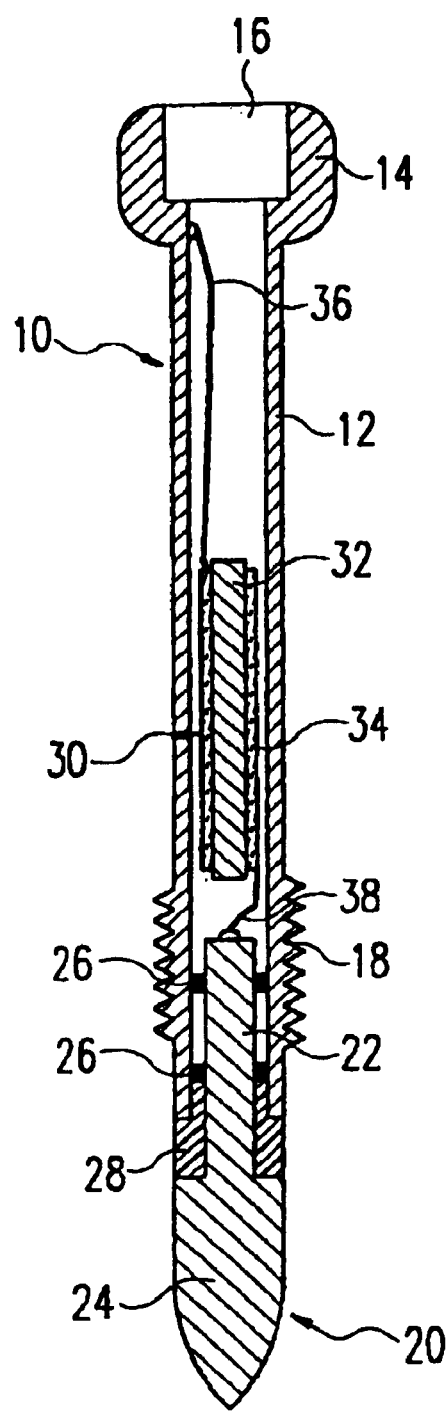

A bone screw 10 is shown in FIG. 1 which comprises a tubular shaft 12 open at both ends and consisting of a biocompatible metal. At one end is an integral head 14. The head 14 has a hexagonal hole or any other configuration for inserting or applying a turning tool. At the end remote of the head 14 or in the vicinity of this end the shaft has an integral self-tapping external thread 18.

An electrically insulated end-piece 20 made of biocompatible metal is mounted in the end of the shaft which is remote of the head 14. The end-piece has an extension 22 in form of a rod, and a tapering front portion 24 the end of which adjacent to the shaft having the same outer diameter as the shaft 12. The extension 22 protrudes into the hollow shaft 12 and is electrically insulated against it by two thin plastic rings 26. A space remains between the front portion 24 and the shaft 12, said space being filled with biocompatible plastic material 28, such as epoxy resin. The surface of the plastic insulation 28 is flush with the surface of the shaft 12 and the adjacent end of the end-piece [24].

A receiving coil 30 having a magnetically soft core 32 and a wire winding 34 is lodged in the interior of the shaft 12. The winding 24 has two terminals 36, 38 which are electrically coupled, e. g. connected by spot welding, to the shaft and the end-piece 20, respectively. Thus, the shaft 12 and the end-piece 20 serve as tissue electrodes. The remaining space within the shaft 12 with exception of the recess 16 is filled with artificial resin not shown for reason of clarity. The space is accessible through the hole of the shaft 12 in the head 14.

Figure 2:
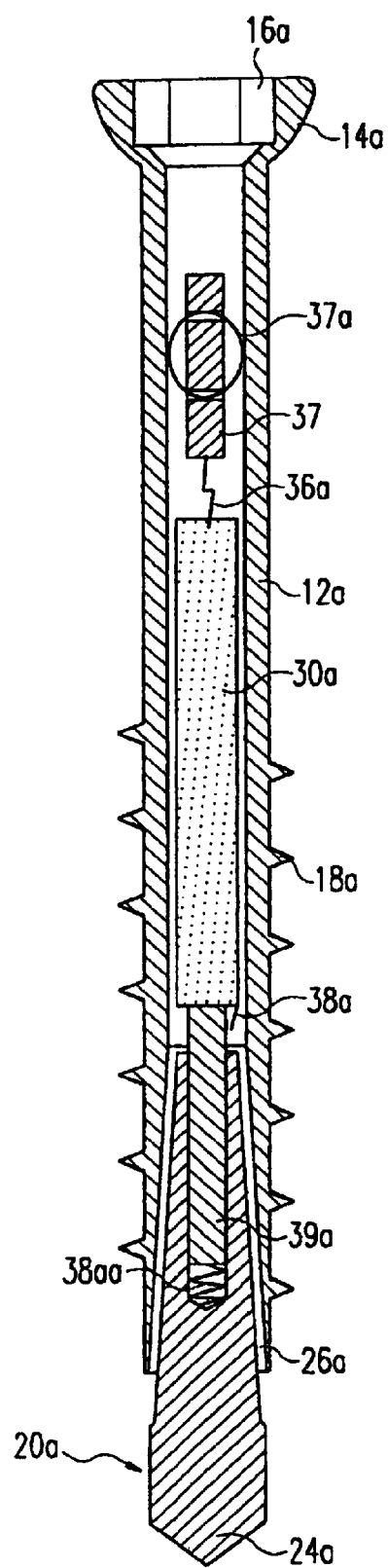
FIG. 2 is a longitudinal section of a second embodiment of the invention which is preferred at present.

The bone screw according to FIG. 2 corresponds essentially to that of FIG. 1, corresponding parts bearing the same reference numbers augmented by an "a". It is therefore sufficient to describe the differences. The terminal wire 36a of the receiving coil 30a is welded to a metal cylinder 37 which has two transverse holes within which a ring-shaped contact spring 37a is mounted which abuts to the inner wall of the shaft 12a. The other terminal 38a of the receiving coil 30a is welded to a portion 39a of the magnet core protruding from the coil winding. A piece of spring wire 38a a sticks in a bore at the front side of the magnet core, making a safe electrical contact with an inner wall of the end piece 20a. The insulation between the shaft 12a and the end-piece comprises a layer 26a of epoxy resin.

Figure 3:
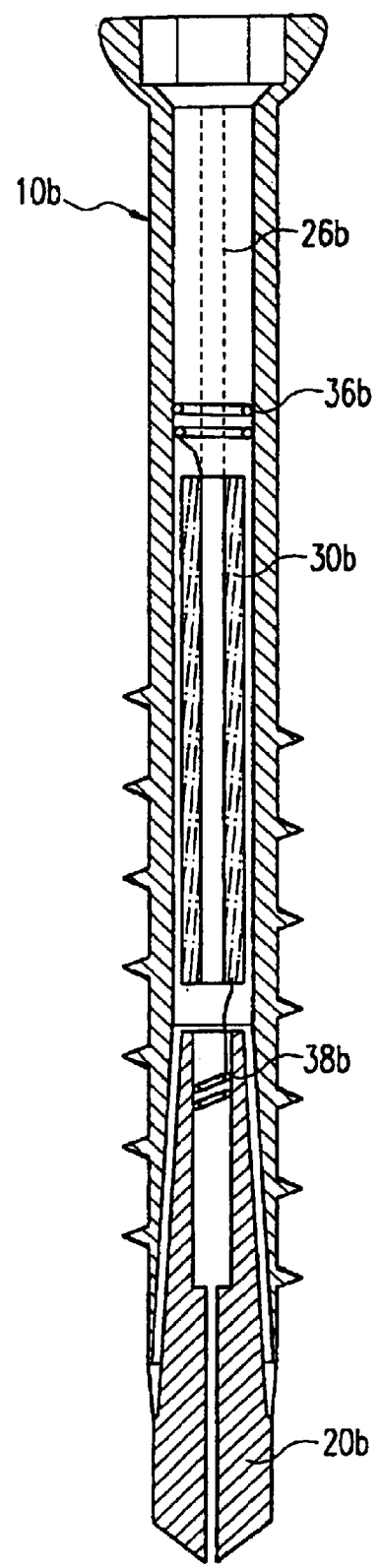
FIG. 3 is a longitudinal section of a further preferred embodiment of the invention.

The embodiment according to FIG. 3 corresponds to a large degree to that according to FIG. 2 with the exception that the bone screw 10b comprises a continuous axial channel through which an thin guide wire can be put. Thus, the channel traverses the insulating filling, as schematically shown at 26b, the receiving coil 30b wound onto a tubular magnet core, and the end-piece 20b. The connecting wires 36b, 38b have helical resilient ends which leave the axial channel free.

Figure 4:
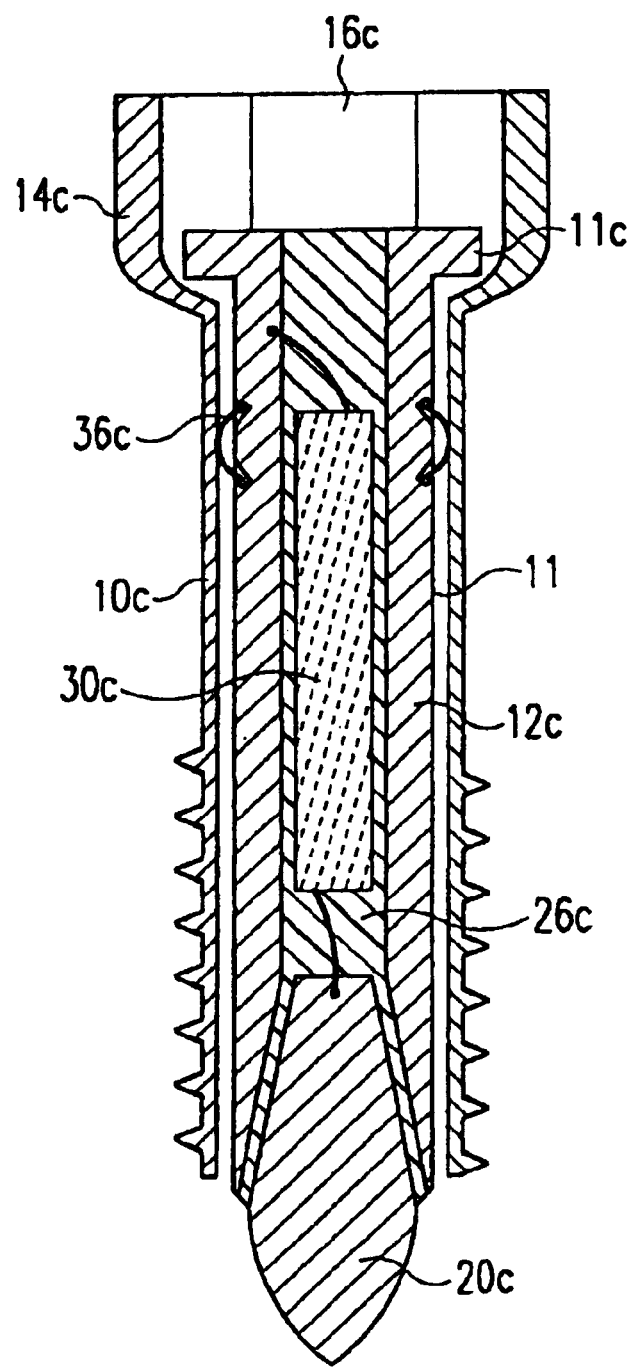
FIG. 4 is a longitudinal section of an embodiment of the invention comprising two parts.

The embodiment of FIG. 4 is similar to that of FIG. 1, however, it comprises two parts, i. e. a tubular bone screw part 10c and an insert 11. The insert 11 has a flat head 11c which fits into the recess 16c, and a shaft 12c which fits into the hollow shaft of the bone screw part 10c. The shaft 12c contains a receiving coil 30c. An electrically insulated end-piece 20c is mounted at the end of the shaft 12c remote of the head 11c. The terminals of the receiving coil 30c are connected to the shaft 12c and the end-piece 20c, respectively. Contact springs are mounted within the shaft 12c which secure an electrical connection between the shaft 12c and the part 10c. In use, first the bone screw part 10c is implanted with the aid of a guide wire and then the "electro"-insert 11 is placed into the hollow bone screw part.

The metal parts can be made of titanium metal or any other known biocompatible metal. An insulating material provided with an electrically conductive material is regarded as equivalent to a metal construction. For example, the end-piece may consist of ceramic material coated with titanium by vapor deposition.

Figure 5:
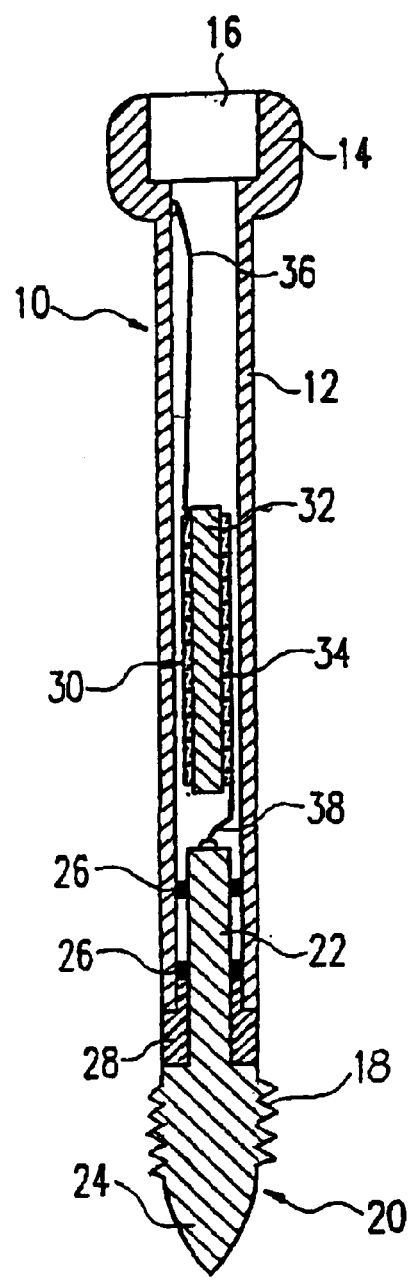
FIG. 5 is a longitudinal section of another embodiment of the invention depicting an external thread positioned on the second tissue electrode protruding from the shaft of the bone screw.

In modified embodiments, the thread extends to the end of the shaft 12 or is provided on the end-piece. As shown in FIG. 5, the end-piece 20 has an integral self-tapping thread 18 disposed on the outer surface thereof intermediate the tapering front portion 24 and the plastic insulation material 28.

What is claimed is:

1. A bone screw comprising
   a tubular shaft made of biocompatible electrically conductive material, forming a first tissue electrode and having at one end a head which has a configuration adapted for engagement by a turning tool;
   a second tissue electrode made of a biocompatible electrically conductive material and positioned at a second end of said shaft remote of said head; electrical insulating means between said shaft and said second tissue electrode;
   a receiving coil mounted within said shaft in which a low-frequency electrical alternating voltage is inducible by means of an external coil, said receiving coil having first and second terminals electrically coupled to said shaft and said second tissue electrode, and
   a bone-screw-type external thread at said second end of said shaft remote of said head.

2. The bone screw according to claim 1, characterized in that said second tissue electrode protrudes from said tubular shaft and tapers with increasing distance from said shaft.

3. The bone screw according to claim 1, characterized in that said external thread is positioned on said second tissue electrode which protrudes from said shaft.

4. The bone screw according to claim 1, characterized in that it has a continuous axial channel.

5. The bone screw according to claim 1, characterized by contact spring means on at least one of the terminals of said receiving coil.

6. A bone screw comprising
   a tubular bone screw part made of a biocompatible electrically conductive material, forming a first tissue electrode, said tubular bone screw part being open at both ends and having at one end a head which has a configuration adapted for engagement by a turning tool and a bone-screw-type external thread proximate the other end of said tubular bone screw part remote from said head;
   an insert part adapted to be inserted into and positioned within said tubular bone screw part, said insert part having a first end which is disposed proximate the head of said tubular bone screw part when the insert part is positioned therein;
   a second tissue electrode made of a biocompatible electrically conducting material and disposed at, and electrically insulated from, a second end of said insert part remote from said first end, wherein said second tissue electrode protrudes through the other end of said tubular bone screw part remote from said head when said insert part is positioned therein; and a receiving coil mounted within said insert part in which a low-frequency electrical alternating voltage is inducible by means of an external coil, said receiving coil having first and second terminals, one of which is electrically coupled to said second tissue electrode and the other of which is electrically coupled to said tubular bone screw part when said insert part is positioned therein.

* * * * *